United States Patent [19]

Brennan et al.

[11] Patent Number: 4,959,069
[45] Date of Patent: Sep. 25, 1990

[54] BRAIDED SURGICAL SUTURES

[75] Inventors: Karl W. Brennan, Somerset; Alison M. Skinner, Long Valley, both of N.J.; Gregory Weaver, New Hope, Pa.

[73] Assignee: Ethicon, Inc., Somerville, N.J.

[21] Appl. No.: 424,622

[22] Filed: Oct. 20, 1989

[51] Int. Cl.$^5$ .............................................. A61B 17/00
[52] U.S. Cl. .................................... 606/228; 428/224; 87/7
[58] Field of Search ............... 606/228, 229, 230, 231, 606/151; 138/123, 129; 139/317; 428/224

[56] References Cited

U.S. PATENT DOCUMENTS

| | | | |
|---|---|---|---|
| 3,035,583 | 5/1962 | Hirsch et al. | 606/223 |
| 3,054,406 | 9/1962 | Usher | 606/151 |
| 3,105,493 | 10/1963 | Usher | 606/231 |
| 3,187,752 | 6/1965 | Glick | 606/231 |
| 3,540,452 | 11/1970 | Usher et al. | 606/231 |
| 3,927,926 | 12/1975 | Powell | 24/115 N |
| 3,949,755 | 4/1976 | Vauquois | 606/229 |
| 4,043,344 | 8/1977 | Landi et al. | 606/230 |
| 4,047,533 | 9/1977 | Perciaccante et al. | 606/230 |
| 4,275,117 | 6/1981 | Crandall | 428/373 |
| 4,510,934 | 4/1985 | Batra | 606/231 |
| 4,550,639 | 11/1985 | Champlin | 87/7 |
| 4,668,318 | 5/1987 | Piccoli et al. | 156/149 |
| 4,804,382 | 2/1989 | Turnia et al. | 623/1 |

Primary Examiner—Randall L. Green
Assistant Examiner—Gary Jackson

[57] ABSTRACT

A braided surgical suture is provided which in a first embodiment is woven in a spiral braid. The suture is braided by moving thread carriers from position to position around a circular path. As each carrier moves it moves from its present position to a succeeding position which is at least two positions removed from its present position. Such spiral braided sutures are advantageously produced without core filaments, providing benefits in strength, smoothness, pliability and cylindrical uniformity without the discontinuity of properties characteristic of conventionally braided cored sutures. In a second embodiment the suture is woven in a lattice braid, providing a plurality of distributed core passageways for individual core fibers.

17 Claims, 4 Drawing Sheets

BRAIDED SURGICAL SUTURES

This invention relates to surgical sutures and, in particular, to braided surgical sutures which obviate the need for a central fiber core.

Surgical sutures may be manufactured in two general forms: monofilaments and multifilaments. Monofilament sutures are generally made of natural materials such as gut, or of extruded polymeric materials such as Nylon, polypropylene, or poly (p-dioxanone), and are highly regarded for their uniform, smooth construction and uniformly distributed tensile strength. However, monofilament sutures generally have the drawback of being fairly rigid and lacking pliability. Multifilament sutures consisting of a plurality of braided filaments of a fine gauge have been found to provide the characteristic of pliability which is often desired by surgeons Such braided sutures may be made of poly(lactide-co-glycolide), polyglycolide, polyester, or silk, for example. But since braided sutures often lack substantial tensile strength, the braided filaments are conventionally braided in a tubular sheath around a core of longitudinally extending threads. Such braided sheath sutures with central cores are shown in U.S. Pat. No. 3,187,752; 4,043,344; and 4,047,533, for example.

Braided sutures with central core threads have been found to exhibit certain disadvantages, however. One is that the tensile strength of the suture is not evenly distributed between the braided sheath and the central core threads. As a consequence, when these sutures are stretched, the sheath and the core will respond differently to the application of the tensile forces. The sheath will respond to the forces independently of the central core threads, causing the central threads to move longitudinally relative to the surrounding sheath. The core threads can also flatten and redistribute themselves within the sheath instead of maintaining the desired rounded cross-sectional shape of the suture. It would be desirable for such tensile forces to be more uniformly distributed throughout the suture, so that all of the fibers of the suture will respond in unison to the tensile forces without distortion of the normal shape of the suture.

Conventionally braided sutures can also feel rough to the touch, due to the changing crossing pattern of the braided filaments, and the interstices formed where the braided fibers overlap and cross each other. To minimize this tactile characteristic it is often necessary to further process the braided suture by heating and stretching the suture. Furthermore, such interstices can trap and retain moisture in a wicking fashion. Retained moisture has been found to be a source of undesired deterioration of sutures made of certain materials, such as absorbable sutures made of poly(lactide-co-glycolide) or polyglycolide, and can also lead to retention of sources of infection within the braid. It would be desirable to form braided sutures which are smoother to the touch, and which do not exhibit interstices or passageways which can trap and retain moisture prior to use of the sutures.

It would further be desirable for braided sutures to match or exceed the breaking strength characteristics of presently available braided sutures with central core threads.

In accordance with the principles of the present invention, a braided suture is provided in which the filaments or threads are braided in a spiral pattern. Sutures braided in a spiral pattern have been found to be capable of maintaining a uniformly rounded cross-sectional shape, and to distribute tensile forces uniformly throughout the braided fibers. Spiral braided sutures also do not form the tube-like structure of the conventional braiding pattern, which eliminates the need for a central fiber core. Since spiral braiding results in an outer sheath pattern in which the braided threads are all flowing in the same direction, the suture is much smoother to the touch than the conventionally braided suture. The smoothly flowing braided configuration also does not provide interstices which can trap undesired moisture in the suture. Furthermore, the spiral braided suture has been found to be stronger, smoother to the touch, and much more pliable than the conventionally braided suture.

In accordance with a further aspect of the present invention a suture is provided which is formed by lattice braiding. The lattice braided suture exhibits a plurality of interwoven threads in a generally rectangular cross-sectional configuration. The lattice braid may be woven around a plurality of core threads distributed in the internal interstices of the lattice network and interlocked into position, unlike the central bundle of core threads of the conventionally braided suture. The lattice braided suture has been found to be superior to the conventionally braided core suture in that it does not exhibit "core pop", the tendency of the core filaments to break through the braided sheath as the suture is bent.

Figure 1A:
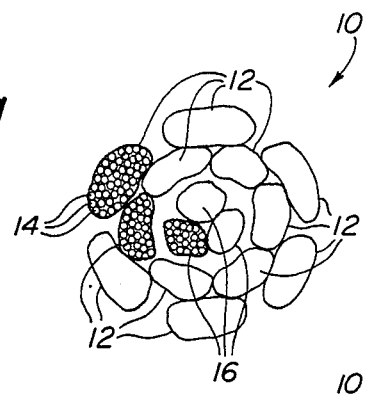
FIGS. 1a and 1b illustrate diagrammatic cross-sectional and side views of a conventionally braided suture.

Referring first to FIGURE 1a, a conventionally braided suture 10 is shown in diagrammatic cross-section. The suture 10 comprises a plurality of threads or carriers 12 which are interwoven to form the braided sheath. Each thread generally comprises a number of individual fibers 14. The braided threads 12 form a tubular sheath around the central core threads 16, which extend longitudinally through the tubular sheath. The sheath is braided using at least three threads, or a greater even number of threads, such as 4, 6, 8, etc. The core may comprise one or any greater number of threads. The suture 10 is shown in FIG. 1a to exhibit its desired cylindrical uniformity. However, it has been found that during handling, heating and stretching of the suture during manufacture the tubular sheath can distort to an oval or oblong shape, with the core threads 16 redistributed in the sheath in an irregular or linear configuration.

As a consequence of the structural independence of the braided sheath and the core threads, the sheath and core will unevenly distribute tensile forces among these two substructures when the suture is stretched, causing the two to move relative to each other. The relative movement of the two can result in the formation of spaces or pockets inside the sheath, between threads 16 of the core and the surrounding sheath. These spaces can entrap moisture through the mechanism of wicking, resulting in premature deterioration and weakening of the suture in in vivo use of the suture.

Figure 2:
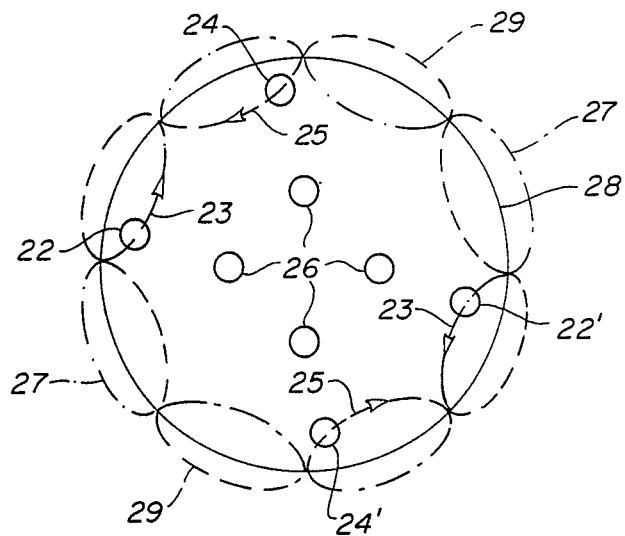
FIG. 2 illustrates the braiding pattern of a conventionally braided suture.

The conventionally braided suture is woven as indicated by the braiding pattern of FIG. 2, shown in a plan view. The individual threads of the braided sheath feed from spools mounted on carriers 22, 22' and 24, 24'. The carriers move around the closed circular loop 28, moving alternately inside and outside the loop 28 to form the braiding pattern. One or more carriers are continually following a serpentine path in a first direction around the loop, while the remaining carriers are following a serpentine path in the other direction. In the illustrated embodiment carriers 22, 22' are travelling around serpentine path 27 in a clockwise direction as indicated by directional arrows 23, and carriers 24, 24' are travelling around serpentine path 29 in a counterclockwise direction as indicated by arrows 25. Disposed within the center of the loop 28 are carriers 26 which dispense the core threads of the suture. Thus, the moving carriers 22, 22', 24, and 24' dispense threads which intertwine to form the braided sheath, and the sheath is formed around the centrally located core threads dispensed from carriers 26. The threads from all of the carriers in a constructed embodiment of FIG. 2 are dispensed upward with respect to the plane of the drawing, and the braided suture is taken up on a reel located above the plane of the drawing.

Figure 1B:
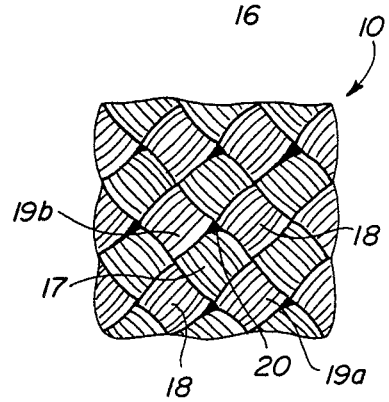

FIG. 1b is an illustration of the outside of the braided sheath of the suture 10 of FIG. 1a, showing the crossing pattern of the braided threads 12. Each thread is composed a number of individual fibers as indicated by the lines on each thread. Where each thread appears on the outside of the sheath it is seen to be orthogonally directed with respect to the thread it crosses over, the thread from beneath which it appears, and the thread it next crosses under. For instance, thread 17 is orthogonally directed with respect to thread 18 on either side of thread 17 where thread 17 crosses over thread 18. The thread 17 is also orthogonally directed with respect to thread 19a from beneath which it appears, and with respect to thread 19b which it next crosses under.

Figure 3:
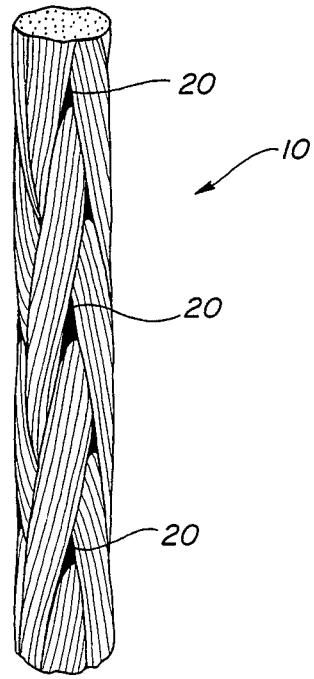
FIG. 3 is a drawing of an enlarged view of the outer sheath of a conventionally braided suture.

This orthogonal crossing relationship of the braided threads results in the formation of small interstices or voids 20 where the threads cross one another, as shown in FIG. 3, which shows a drawing reproduction of an enlarged photograph of a conventionally braided suture. These voids 20 can entrap moisture which can lead to premature deterioration of the suture, and can also entrap bacteria and other sources of infection causing complication of wound healing.

Figure 4A:
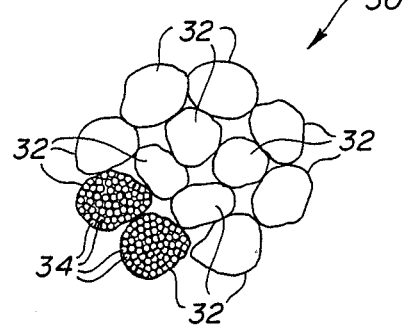
FIGS. 4a and 4b illustrate diagrammatic cross-sectional and side views of a spiral braided suture of the present invention.

Referring now to FIG. 4a, a spiral braided suture 30 of the present invention is shown in diagrammatic cross-section. The braided suture 30 comprises a plurality of interwoven and interlocked threads 32, each of which may comprise a number of individual fibers 34. Due to the interlocking of the threads 32, no central passageway is formed in which moisture can become entrapped. The interlocking of the threads also causes the threads to move in unison as a continuous structure, thereby uniformly distributing tensile forces when the suture 30 is pulled or stretched.

Figure 4B:
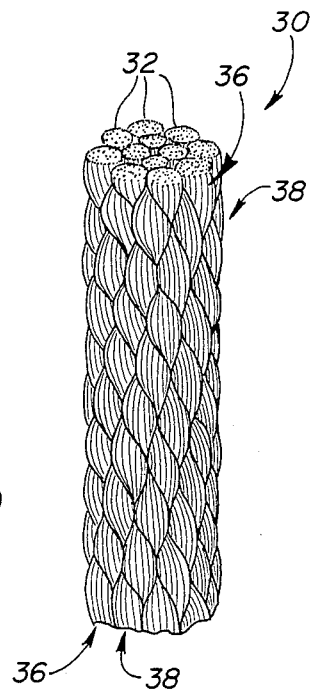

The spiral pattern of the suture 30 is clearly shown in the outside view of the suture of FIG. 4b. The threads on the outside are seen to be aligned in a spiral pattern which ascends from the lower left to the upper right in the drawing as the outer threads precess around the outer surface of the suture. One spiraling set of threads is indicated between arrows 36, and another set is indicated between arrows 38. As the pattern spirals, individual threads on the outer surface are in a parallel orientation with respect to each other and with respect to the longitudinal length of the suture as they continually reappear in the spiral pattern.

With all threads aligned in the parallel, offset spiral pattern of FIG. 4b, it may be seen that there are no voids or interstices formed on the outside surface of the suture. This is due to the parallel orientation of the threads, as opposed to the orthogonally directed crossing pattern of the threads of the conventionally braided suture of FIGS. 1b and 3. The parallel orientation of the outer appearing threads also provides a smoother feel to the suture, since the hand will sense the continuous, longitudinal orientation of the parallel threads as it is run along the suture.

Figures 5A, 5B:
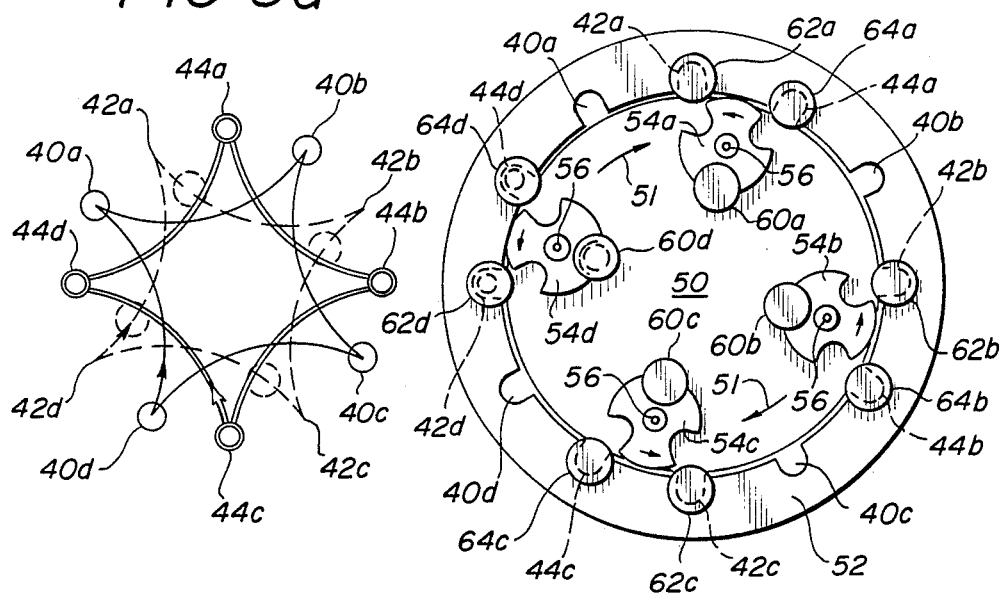
FIG. 5a illustrates the braiding pattern of a spiral braided suture of the present invention.
FIG. 5b is a diagrammatic plan view of a mechanism used to braid a spiral braided suture of the present invention.

A spiral braided suture of the present invention is formed of four or more interwoven threads. Preferably at least nine threads are braided in groups of three, and a braiding pattern for a spiral braided suture of twelve threads, arranged in groups of four, is shown in FIG. 5a. In the illustrated pattern the carriers move sequentially in the same direction around the circular loop of carriers. As they move, each carrier moves from its present position to a succeeding position which is at least two positions removed from its present position. In the illustration of FIG. 5a, each carrier moves to the third succeeding position around the loop. The twelve carriers are grouped into three groups of four carriers each. In the first group, carriers move in unison between positions 42a, 42b, 42c, and 42d. The carrier at position 42a moves to position 42b, passing by positions 44a and 40b as it does so. As it moves, the carrier at position 42b is moving to position 42c, bypassing positions 44b and 40c. At the same time the carrier at position 42c is moving to position 42d, and the carrier at position 42d is moving to position 40a.

After these four carriers have moved to their new positions in unison, the carriers at positions 44a, 44b, 44c, and 44b move to their succeeding positions. Then the carriers at positions 40b, 40c, 40d, and 40a move to their succeeding positions. The sequence then repeats in the same fashion.

Apparatus for executing the spiral braiding pattern of FIG. 5a is diagrammatically shown in FIG. 5b. The apparatus comprises a rotating central platform 50 which is surrounded by an annular plate 52. The platform 50 rotates as indicated by arrows 51. Pivotally mounted on the platform 50 are four rotating carrier pickups 54a, 54b, 54c, and 54d which rotate about pivot points 56. Each pickup has a number of apertures which engage the carriers to move them to their succeeding positions, the number being chosen in correspondence with the number of positions to be bypassed as the carriers move in their braiding pattern. In the illustrated embodiment the number of apertures is three, enabling the carriers to bypass two positions each time they are moved. The twelve carrier positions are delineated by rounded openings in the annular plate 52, four of which are indicated at 40a, 40b, 40c, and 40d. The carriers which carry spools of thread are indicated at 60, 62, and 64.

In operation pickup 54a will engage the carrier 60a at position 40a. As the central platform 50 rotates the pickup 54a simultaneously rotates to transfer the carrier 60a from position 40a to position 40b, which has just been vacated by carrier 60b. The carrier 60a is seen to bypass carriers 62a and 64a as it travels to its succeeding position 40b. As carrier 60a is transferred by pickup 54a, pickups 54b, 54c, and 54d simultaneously are transferring carriers 60b, 60c, and 60d to their succeeding positions.

As the pickup 54a is about to deposit the carrier 60a at position 40b, the pickup engages carrier 64a to begin transferring that carrier to its succeeding position. The carriers 64b, 64c, and 64d are similarly engaged simultaneously by the other three pickuPs. After the carriers 60a, 60b, 60c, and 60d have been deposited at their new positions and the carriers 64a, 64b, 64c, and 64d are enroute to their succeeding positions, the pickups engage the carriers 62a, 62b, 62c, and 62d for transfer. As this sequence of carrier transfer continues, threads from the spools on the carriers are dispensed upward with respect to the plane of the drawing and the braided suture is taken up on a reel located above the apparatus.

Figures 6A, 6B:
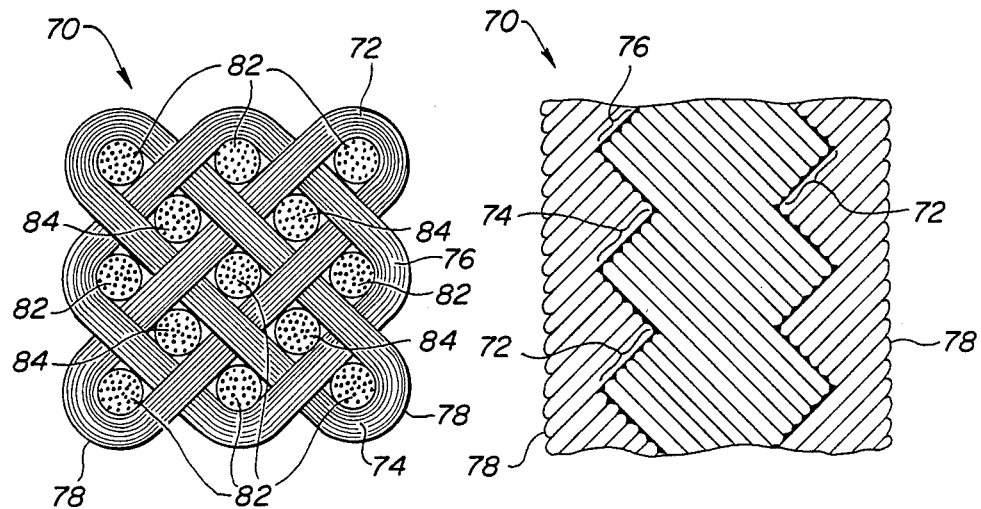
FIGS. 6a and 6b illustrate the braiding pattern and outside sheath of a lattice braided suture of the present invention.

A lattice braided suture 70 of the present invention is shown in FIG. 6a, which schematically illustrates the structure of the lattice braid. In FIG. 6a, three or more threads are braided in a lattice pattern. One thread or group of threads traverses the path 72, a loop extending from the upper right to the lower left of the drawing. As the carrier or carriers dispensing thread on path 72 move around this path, they alternately cross over and under the paths of the other threads that they encounter, the crossing pattern being determined by the times and locations of travel of the respective carriers. In a similar fashion a second carrier or carriers dispensing thread traverse a path 74 from the lower right to the upper left of the pattern. Like the first path, the thread dispensed from carriers travelling this path alternately crosses over and under the other paths it encounters. A third path 76 travels around the intersection of the first path 72 and the second path 74. Like the first two paths, the thread dispensed from the carrier or carriers traversing path 76 alternately crosses over and under the threads of the other paths it encounters.

The lattice braid of FIG. 6a is seen to exhibit a generally square shape in cross-section with rounded corners. While the lattice braided suture has been found to provide less tensile strength than the spiral braided suture, the lattice braided suture can be strengthened by the inclusion of individual core threads running longitudinally through the interlocking lattice. A number of core threads may be located at the positions indicated at 82 in the lattice, at the positions indicated at 84, or both. This uniform distribution of core threads throughout the lattice, which results in secure capture of the individual threads within the loops of the lattice, has been found to provide a uniform distribution of tensile forces throughout the suture.

The outside of the lattice braided suture 70 is illustratively shown in FIG. 6b. The outer threads of the lattice are seen to be distributed in an angularly offset, generally parallel configuration. The drawing shows the generally parallel alignment of threads 72, 74, and 76 on the outside of the suture, forming a substantially smooth, longitudinally extending outer thread surface on each side of the square configuration. The rounded corners 78, shown on each side of the drawing, are also seen to smoothly extend along the length of the suture.

Figure 7:
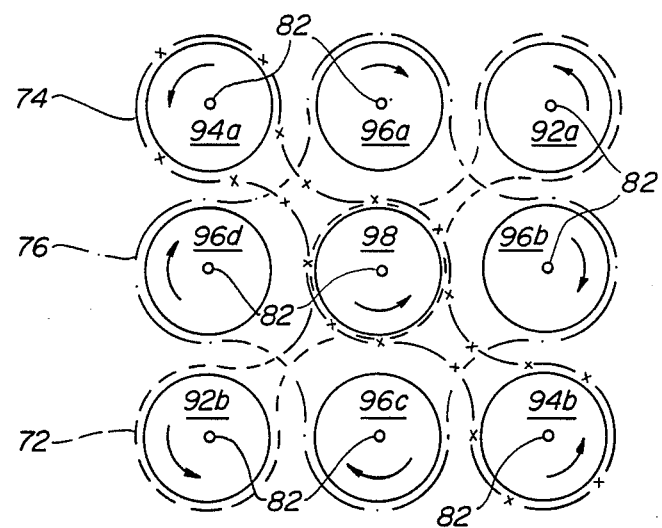
FIG. 7 is a diagrammatic plan view of a mechanism used to braid a lattice braided suture of the present invention.

Apparatus for braiding the lattice braided suture of FIG. 6a is schematically shown in FIG. 7. The apparatus includes a plurality of rotating discs which transfer the carriers around and along their intended paths of travel. In a preferred embodiment there are three carriers traversing each path. Extending through the center of each rotating disc is a core thread 82, each of which becomes engaged in the lattice loops formed around its respective disc. The path 72 is traversed by carriers which rotate around disc 92a and are then transferred to the central disc 98. Each carrier travels halfway around disc 98 and is then transferred to disc 92b. The carriers travel around disc 92b and back to the central disc 98. After travelling around the other side of disc 98 each carrier is transferred back to rotating disc 92a and its starting point.

In a similar manner a second group of carriers on the path 74 travel around disc 94a and are transferred to the central disc 98. After travelling halfway around disc 98 each carrier is transferred to disc 94b. Each carrier travels around the rotating disc 94b, back to the other side of the central disc 98, and is returned to disc 94a and its starting point.

The third path 76 passes around rotating discs 96a, 96b, 96c, and 96d. The carriers which travel this path 76 pass around three-quarters of each disc before being transferred to the succeeding disc in the loop. As each carrier traverses the path 76 it is seen to pass inside the end discs of the other two paths 72 and 74, thereby enclosing the intersection of these two paths at the central disc 98.

The apparatus of FIG. 7 may be operated with a plurality of carriers travelling each path simultaneously. For instance, the apparatus may be operated with three carriers on each path to form a lattice braid of 9 threads. Alternatively each path may include 4 carriers for a total of 12 braided threads. As a third example, the apparatus may operate with 6 carriers on each path for a total of 18 threads in the braided suture.

Spiral braided sutures of the present invention can be expected to provide a 20% improvement in smoothness over conventionally braided sutures, a 20% improvement in pliability, and a 50% improvement in cylindrical uniformity. The improvement in smoothness is due to the parallel alignment of the suture threads on the outside of the spiral braided suture. The improvement in pliability is due to the thread crossovers of the spiral braid, which enhances fiber mobility; the individual threads in the spiral braided suture will easily move relative to each other as the suture is bent. And since there is no core to become misaligned or misshapen, cylindrical uniformity is improved.

Improvements in breaking strength can also be expected for the spiral braided suture. In a test of breaking strength remaining (BSR) after 21 days of in vivo use of an absorbable suture of conventional braid, typically 40–50% of the breaking strength remains. A 15–20% improvement in BSR can be expected in use of a spiral braided suture of the present invention under the same conditions.

The lattice braided suture provides the capability of producing a high quality composite suture, in which advantage is taken of the different characteristics of one type of material for the braid and another type of material for the core threads. As discussed above, the lattice braided suture is substantially more immune to the problem of core pop than the conventionally braided suture, since the core threads are distributed throughout the structure of the braid and are not positioned in a single central location. Both the spiral and lattice braided sutures have been found to exhibit less surface area exposed to ambient conditions, and hence less exposure to moisture, than conventionally braided sutures.

What is claimed is:

1. A braided surgical suture in which a plurality of surgically compatible filaments are woven in a spiral braid by moving filament dispensers to different positions around a closed loop, wherein an individual dispenser in the loop is moved from its current position to a succeeding position which is at least two positions removed from said current position.

2. The braided surgical suture of claim 1, wherein the number of filaments is at least nine.

3. The braided surgical suture of claim 2, wherein said filament dispensers move around said loop in the same direction.

4. The braided surgical suture of claim 3, wherein said filament dispensers are organized in three uniformly distributed groups around said loop and the dispensers in each group move around said loop in unison.

5. The braided surgical suture of claim 3, wherein the number of filaments is twelve and wherein an individual dispenser in the loop is moved from its current position to a succeeding position which is three positions removed from said current position.

6. The braided surgical suture of claim 1, wherein the portions of said filaments which are visible on the outside of said braided suture are oriented substantially parallel to each other and are distributed in patterns which spiral around the outside of said suture.

7. The braided surgical suture of claim 1, wherein said surgically compatible filaments are woven in a spiral braid without any central, longitudinally extending core filaments.

8. A braided surgical suture in which a plurality of surgically compatible filaments are woven in a lattice braid by moving filament dispensers in three closed loop paths, a first and second of said paths being generally oblong and crossing over each other at a central intersection, and the third of said paths passing through the ends of said first and second paths outside said central intersection.

9. The braided surgical suture of claim 8, wherein said suture in cross-section exhibits a generally rectangular shape, with filaments traversing said ends of said first and second paths being located at the corners of said rectangular shape.

10. The braided surgical suture of claim 8, wherein each moving filament dispenser alternately passes over then under the filaments dispensed on the paths it intersects.

11. The braided surgical suture of claim 10, wherein there are at least three filament dispensers traversing each of said paths.

12. The braided surgical suture of claim 8, wherein there are formed a plurality of core fillament passageways located adjacent to the points of intersection of two or more of said paths.

13. The braided surgical suture of claim 12, further comprising at least four core filaments located in ones of said passageways.

14. The braided surgical suture of claim 13, wherein said core filaments are symmetrically distributed with respect to said point of intersection.

15. The braided surgical suture of claim 13, wherein said core filaments are made of a different surgically compatible material than that of said woven filaments.

16. The braided surgical suture of claim 12, further comprising at least nine core filaments located in ones of said passageways.

17. The braided surgical suture of claim 12, further comprising at least thirteen core filaments located in ones of said passageways.

* * * * *